United States Patent [19]

Bartek et al.

[11] 4,115,464

[45] Sep. 19, 1978

[54] PROCESS FOR PREPARING DIARYLETHYLENES

[75] Inventors: Joseph P. Bartek, University Hts.; Serge R. Dolhyj, Parma; Louis J. Velenyi, Lyndhurst; Robert K. Grasselli, Chagrin Falls, all of Ohio

[73] Assignee: The Standard Oil Company, Cleveland, Ohio

[21] Appl. No.: 792,638

[22] Filed: May 2, 1977

[51] Int. Cl. ................................................ C07c 5/42
[52] U.S. Cl. ........................ 260/668 C; 260/669 R; 260/669 B; 260/680 E
[58] Field of Search ........... 260/668 C, 669 R, 669 B, 260/680 E

[56] References Cited

U.S. PATENT DOCUMENTS

| | | | |
|---|---|---|---|
| 3,308,196 | 3/1967 | Bajars | 260/669 R |
| 3,396,205 | 8/1968 | Alexander et al. | 260/680 E |
| 3,739,038 | 6/1973 | Franz et al. | 260/668 C |
| 3,845,156 | 10/1974 | Farha | 260/680 E |
| 3,933,932 | 1/1976 | Vrieland et al. | 260/669 R |

*Primary Examiner*—Delbert E. Gantz
*Assistant Examiner*—C. E. Spresser
*Attorney, Agent, or Firm*—Evelyn R. Kosman; Herbert D. Knudsen; Larry W. Evans

[57] ABSTRACT

This invention relates to an improved process for the dehydrogenation of diarylethanes to the corresponding diarylethylenes in the presence of oxygen and in the presence of a metal phosphate catalyst.

13 Claims, No Drawings

PROCESS FOR PREPARING DIARYLETHYLENES

BACKGROUND OF THE INVENTION

The preparation of diarylethylenes by the dehydrogenation of 1,1-diarylethane has been reported in U.S. Pat. Nos. 2,450,334 and 3,071,360. U.S. Pat. No. 2,450,334 specifically describes the dehydrogenation of 1,1-di-p-tolylethane to 1,1-di-p-tolylethylene in the presence of steam and in the presence of a catalyst containing metals having atomic numbers of from 23 to 29, and their mixtures. U.S. Pat. No. 3,071,630 describes the dehydrogenation in the absence of oxygen of 1,1-diphenylethane to 1,1-diphenylethylene and to 1,2-diphenylethylene (stilbene) in the presence of a chromium-alumina catalyst. However, the process of the present invention comprising the oxydehydrogenation of the 1,1-diaryl-or the symmetrical 1,2-diarylethanes to the corresponding diarylethylenes in the presence of a metal phosphate catalyst, wherein greatly improved yields and selectivities to the desired products can be realized, has heretofore not been described.

The diarylethylenes are of particular interest for use in the preparation of, among others, dyes and pharmaceuticals, and as monomers in the formation of novel polymeric compositions. Thus an economically feasible process for the manufacture of these starting materials is in demand.

SUMMARY OF THE INVENTION

The present invention comprises the process for the oxydehydrogenation of the diarylethanes to the corresponding diarylethylene compounds. The diarylethane compounds contemplated to be within the scope of this invention include 1,1-diphenylethane, 1,2-diphenylethane, and the corresponding mono- and multi- methyl-nuclear-substituted derivatives, such as, the 1,1-ditolylethanes, 1,2-ditolylethanes and the xylyl-ethanes. The process comprises passing a gaseous mixture of molecular oxygen such as air and the diarylethane compound in the presence or absence of a diluent such as steam, carbon dioxide, nitrogen or an inert hydrocarbon, over a catalyst at a temperature of from about 250° to 650° C, said catalyst being a metal phosphate represented by the empirical formula:

$$M_b M^1_a P_x O_y$$

wherein
M is at least one element selected from the group consisting of bismuth, antimony, iron, nickel, cobalt, chromium, lanthanum, cerium, uranium, tin, calcium or magnesium;
$M^1$ is one or more elements of the group germanium, lead, molybdenum, tungsten, strontium, barium, arsenic, manganese, rhenium, thorium, the rare earths, except lanthanum and cerium, the metals of Groups 1A, 1B, IIB, IIIA, or VB of the Periodic Classification of elements;
P is phosphorus; and
wherein
$a$ is a number from 0.1 to 10;
$b$ is a number from 0 to 10;
$x$ is a number from 0.5 to 10; and
$y$ is the number of oxygens required to satisfy the valence requirements of the other elements present.

The phosphate oxyanion may be a monomeric or polymeric, including the pyrophosphate structure.

The catalysts useful in the instant process may be used alone or supported on a carrier. Suitable carrier materials include silica, alumina, alundum, titania, zirconia and mullite, and particularly phosphate-type carriers such as zirconium phosphate, aluminum phosphate, antimony phosphate, baron phosphate or others that are known in the art. In general, the support may be employed in amounts less than 95% by weight of the final catalyst composition, and the catalyst may be incorporated in the carrier by coating, impregnation or coprecipitation.

These catalysts may be prepared by coprecipitation or by other methods known in the art. Generally they are prepared by mixing an aqueous solution of the metal nitrates with an aqueous solution of ammonium dihydrogen phosphate or by precipitating the metal-salt solutions with phosphoric acid followed by drying the precipitate.

The catalyst may be calcined to produce desirable physical and chemical properties such as attrition resistance, optimum surface area, particle size and the development of an active catalyst phases. It is generally preferred that the calcined catalyst be further heat-treated in the presence of oxygen at a temperature of above 250° C but below a temperature deleterious to the catalyst.

The reaction may be conducted in a fixed-bed or a fluidized-bed reactor at temperatures as low as 250° C, although optimum temperatures for the dehydrogenation reaction are in the range of from about 350° to about 550° C, and there is no apparent advantage in operating at temperatures much in excess of 650° C.

The pressure at which the present process is usually conducted is about atmospheric, although pressure of from slightly below atmospheric up to and above 3 atmospheres are operable.

The apparent contact time employed in the instant process may be within the range of 0.1 to about 20 seconds, and for good selectivity and yields a contact time of from 1 to 5 seconds is preferred.

The molar ratio of oxygen to diarylethane compound fed to the reactor can range from about 0.1 to about 200 moles of oxygen per mole of the diarylethane, but a preferred range is from about 0.5 to about 100 moles of oxygen per mole of aromatic compound. The oxygen employed may be in the form of pure oxygen, although the use of air is preferred for purposes of convenience.

Diluents such as steam, carbon dioxide, nitrogen, inert hydrocarbons or other inert gases may also be used, and amounts of from about 1 to 100 volumes of diluent per volume of diarylethane compound are suitable.

The following examples serve to illustrate the feasibility and the improvement obtained in the oxydehydrogenation process of the present invention utilizing phosphate catalysts.

SPECIAL EMBODIMENTS

Examples 1–11 are representative of the present invention.

CATALYST PREPARATIONS

Example 1 — 

A mixture of 276.5 g of Co (NO$_3$)$_2$. 6H$_2$O 20.2 g of Fe (NO$_3$)$_3$. 9H$_2$O and 48.5g of Bi (NO$_3$)$_3$ . 5H$_2$O was added to a solution of 138g of $(NH_4) H_2PO_4$ in 100cc of water. A purple-colored slurry formed which changed to a blue color on drying. The catalyst was denitrified by heating for 3 hours at 290° F and 3 hours at 427° F and calcined at 555° F for 3 hours.

Example 2 — $Co_9 La_1 Bi_1 P_{12} O_x$ 131g of $Co(NO_3)_2 \cdot 6H_2O$ were dissolved in 400cc of distilled water. To this solution were added 21.65g of $La(NO_3)_3 \cdot 6H_2O$ and 24.25g of $Bi(NO_3)_3 \cdot 5H_2O$. 69.2g of 85% $H_3PO_4$ were slowly added to this mixture which resulted in the formation of a purple precipitate. The mixture was evaporated to a paste and dried overnight at 110° C, then calcined for 3 hours at 277° C, and for 3 hours at 550° C.

Example 3 — $Co_9 Cr_1 Bi_1 P_{12} O_x$ 131g of $Co(NO_3)_2 \cdot 6H_2O$ and 5.0g of $CrO_3$ were dissolved in 600cc of distilled water. 24.25g of $Bi(NO_3)_3 \cdot 5H_2O$ were added to this solution and a brown precipitate formed. 69.2g of 85% $H_3PO_3$ were slowly added to the solution and which resulted in the formation of additional precipitate. The solution was evaporated to a paste and the paste was dried overnight at 110° C. The catalyst was then calcined at 277° C for 3 hours and then at 550° C for 3 hours.

Example 4 — $Co_9 Fe_1 Bi_1 P_{12} O_x$ 131g of $Co(NO_3)_2 \cdot 6H_2O$ were dissolved in 400cc of distilled water. 20.2g of $Fe(NO_3)_3 \cdot 9H_2O$ and 24.25g of $Bi(NO_3)_3 \cdot 5H_2O$ were added to this solution. This was followed by the slow addition of 69.2g of 85% $H_3PO_4$ to the solution which resulted in the formation of a pink precipitate. The solution was evaporated to a purple paste, dried overnight at 110° C, and calcined for 3 hours at 277° C and for 3 hours at 550° C.

Example 5 — $Co_7 Fe_3 P_{12} O_x$ 101.87g of $Co(NO_3)_2 \cdot 6H_2O$ and 60.6g of $Fe(NO_3)_3 \cdot 9H_2O$ were dissolved in 400cc of distilled water. 69.2g of 85% $H_3PO_4$ were then added. The solution was evaporated to a purple paste, dried overnight at 110° C and calcined for 3 hours at 277° C and for 3 hours at 550° C.

Example 6 — $Ca_8 Ni_1 P_{12} O_x$ 94.46g of $Ca(NO_3) \cdot 4H_2O$ and 14.54g of $Ni(NO_3)_2 \cdot 6H_2O$ were dissolved in 600cc of distilled water. To this was added 69.2g of 85% $H_3PO_4$. The solution was evaporated to a light green paste and dried overnight at 110° C. The catalyst was then calcined for 3 hours at 277° C and then for 3 hours at 650° C.

Example 7 — $Sn_9 P_{12} O_x$

A slurry of 67.8g of $SnO_2$ was prepared in 600cc of distilled water. 69.2g of 85% $H_3PO_4$ were added and the solution was heated to boiling for an hour. The solution was then evaporated to a white paste, dried overnight at 110° C, and calcined for 3 hours at 650° C.

Example 8 — $K_{3.6} Ni_{34.8} Sn_{31.2} P_{12} O_x$ 63.25g of $SnCl_4 \cdot 5H_2O$ were added to 200cc of distilled water. $NH_3$ was added until no further precipitate formed. The resulting gel was filtered and washed with distilled water and then added to a solution of 58.45g of $Ni(NO_3)_2 \cdot 6H_2O$ in 200cc of water. 6.88g of 85% $H_3PO_4$ were slowly added to the mixture followed by the addition of a solution of 1.17g of KOH in 50cc of water. The mixture was evaporated to a paste, dried overnight at 100° C and calcined for 4 hours at 600° C.

Example 9 — $Mg_9 Fe_1 Bi_1 P_{12} O_x$ 115.38g of $Mg(NO_3)_2 \cdot 6H_2O$ and 20.2g of $Fe(NO_3)_3 \cdot 9H_2O$ were dissolved in 400cc of distilled water. 24.25g of $Bi(NO_3)_3 \cdot 5H_2O$ were added and a white precipitate formed. Additional precipitate formed with the slow addition of 69.2g of 85% $H_3PO_4$. The mixture was heated to boiling and evaporated to a white paste. The paste was dried overnight at 110° C, and calcined for 3 hours at 277° C and for 3 hours at 550° C.

Example 10 — $K_{2.4} Ni_{74.4} Sn_{13.2} Sb_{3.6} P_{12} O_x$

The preparation was the same as in Example 8 with the exception that 8.0g of 85% $H_3PO_4$ was added to the nickel-tin mixture.

The above catalyst compositions were employed in the oxydehydrogenation of 1,1-diphenylethane and 1,2-diphenylethane to form the corresponding 1,1-diphenylethylene and 1,2-diphenylethylene, respectively, in a fixed-bed reactor having a catalyst volume capacity of 20cc or 40cc. The reactor was equipped with stainless steel evaporizer blocks or that liquid feeds could be introduced directly into the reactor. Air and optionally nitrogen was introduced by means of calibrated rotameters, and the diarylethane compound was pumped directly into the reactor as a solvent soltuion of 5–11 percent by weight of the diaryl compound in benzene. The tops of the downflow reactors were packed with inert Alundum particles which served as an evaporization zone. The reactor contained 5cc or 10cc of Alundum and 15cc or 30cc of catalyst depending on the reactor volume.

The products were scrubbed from liquid materials at the reactor exit in two acetone traps (second kept at 0° C). The liquid products were quantitatively analyzed using H-P gas chromatograph equipped with 2m. 5% Carbowax on Haloport-F (col. "B-1"). The Column was kept isothermally at 170° C. Quantitative standardization was obtained using a known concentration of the diarylethylene compound in acetone.

The reactor was maintained at a temperature in the range of 375°–475° C and at atmospheric pressure. Molar ratios of air to hydrocarbon of from 85-220 were employed and the contact time was about 3 seconds. Particle size of the catalyst employed was 10/30 mesh. The percent per pass conversion to the desired diphenylethylene compound and the selectivity of the reactions reported in the table were calculted in the following manner:

Percent Conversion =
$$\frac{\text{Moles carbon of diarylethane converted}}{\text{Moles carbon of diarylethane fed}} \times 100$$

Percent Single Pass Yield =
$$\frac{\text{Moles carbon of diarylethylene obtained}}{\text{Moles carbon of diarylethane fed}} \times 100$$

Percent Selectivity =
$$\frac{\text{Moles carbon of diarylethylene obtained}}{\text{Moles carbon of diarylethane converted}} \times 100$$

TABLE

Oxydehydrogenation of 1,1-Diphenylethane

TABLE-continued

| Example No. | Catalyst | Mol Ratio air/H.C. | Reaction Temp °C | Mol % Total Conv. | Mol % Per Pass Conversion* to | |
|---|---|---|---|---|---|---|
| | | | | | 1,1-Diphenylethylene | Select. to 1,1-Diphenylethylene |
| 1 | $Co_{9.5}Fe_{0.5}BiP_{12}O_x$ | 105 | 425 | 92.0 | 77.5 | 84.2 |
| 2 | $Co_9LaBiP_{12}O_x$ | 122 | 450 | 94.7 | 67.6 | 71.7 |
| 3 | $Co_9CrBiP_{12}O_x$ | 138 | 450 | 88.9 | 63.7 | 76.3 |
| 4 | $Co_9FeBiP_{12}O_x$ | 220 | 375 | 69.0 | 60.3 | 87.3 |
| 5 | $Co_7Fe_3P_{12}O_x$ | 122 | 425 | 79.6 | 54.8 | 69.7 |
| 6 | $Ca_8NiP_{12}O_x$ | 220 | 475 | 75.3 | 52.3 | 69.4 |
| 7 | $Sn_9P_{12}O_x$ | 220 | 450 | 52.4 | 38.4 | 73.4 |
| 8 | $K_{3.6}Ni_{34.8}Sn_{31.2}P_{12}O_x$ | 85 | 429 | 81.9 | 32.1 | 39.2 |
| 9 | $Mg_9FeBiP_{12}O_x$ | 220 | 450 | 33.1 | 17.3 | 52.3 |
| 10 | $K_{2.4}Ni_{74.4}Sn_{13.2}Sb_{3.6}P_{12}O_x$ | 85 | 419 | 84.1 | 11.2 | 13.4 |
| Oxydehydrogenation of 1,2-Diphenylethane | | | | | Stilbene | Select. to Stilbene |
| 11 | $Co_{9.5}Fe_{0.5}BiP_{12}O_x$ | 132 | 400 | 91.7 | 74.3 | 81.1 |

*corrected to 100% carbon balance.

We claim:

1. A process for the dehydrogenation of diarylethanes to the corresponding diarylethylenes wherein said diarylethane is selected from the class consisting of 1,1-diphenylethane, 1,2-diphenylethane, and their methyl nuclear-substituted derivatives, the process comprising passing a gaseous mixture of the diarylethane, molecular oxygen and optionally a diluent gas, over a catalyst at a temperature of from about 250° to 650° C, said catalyst having the compositon represented by the empirical formula:

$$M_a M^1_b P_x O_y$$

wherein
M is at least one element selected from the group consisting of bismuth, antimony, iron, nickel, cobalt, chromium, lanthanum, cerium, uranium, tin, calcium or magnesium;
$M^1$ is one or more elements of the group germanium, lead, molybdenum, tungsten, strontium, barium, arsenic, manganese, rhenium, thorium, the rare earths, except lanthanum and cerium, the metals of Groups 1A, 1B, IIB, IIIA, or VB of the Periodic Classificaton of elements;
P is phosphorus; and
wherein
a is a number from 0.1 to 10;
b is a number from 0 to 10;
x is a number from 0.5 to 10; and
y is the number of oxygens required to satisfy the valence requirements of the other elements present.

2. The process in claim 1 wherein 1,1-diphenylethane is converted to 1,1-diphenylethylene.

3. The process in claim 1 wherein 1,2-diphenylethane is converted to 1,2-diphenylethylene.

4. The process in claim 1 wherein 1,1di-tolylethanes are converted to 1,1-di-tolylethylenes.

5. The process in claim 1 wherein 1,2-di-tolylethanes are converted to 1,2-di-tolylethylenes.

6. The process in claim 1 wherein the molar ratio of oxygen to diarylethane compound is in the range from about 0.5 to 100.

7. The process in claim 6 wherein the reaction temperature is in the range of from about 350° to 550° C.

8. The process in claim 7 wherein the apparent contact time is from about 0.1 to 20 seconds.

9. The process in claim 8 wherein M in the catalyst formula consists of the combination of cobalt, iron and bismuth.

10. The process in claim 8 wherein M in the catalyst formula consists of the combination of cobalt, lanthanum and bismuth.

11. The process in claim 8 wherein M in the catalyst formula consists of the combination of cobalt, chromium and bismuth.

12. The process in claim 9 wherein $M^1$ in the catalyst formula is potassium.

13. The process in claim 10 wherein $M^1$ in the catalyst formula is cadmium, and nickel is substituted for cobalt.

* * * * *